US008700209B2

(12) United States Patent
DiMaggio

(10) Patent No.: US 8,700,209 B2
(45) Date of Patent: Apr. 15, 2014

(54) METHOD AND SYSTEM FOR ELECTRONIC ASSISTANCE IN DISPENSING PHARMACEUTICALS

(75) Inventor: John P DiMaggio, Powell, OH (US)

(73) Assignee: Omnicare, Inc., Covington, KY (US)

( * ) Notice: Subject to any disclaimer, the term of this patent is extended or adjusted under 35 U.S.C. 154(b) by 1640 days.

(21) Appl. No.: 11/384,554

(22) Filed: Mar. 20, 2006

(65) Prior Publication Data

US 2006/0161298 A1 Jul. 20, 2006

Related U.S. Application Data

(62) Division of application No. 10/610,681, filed on Jul. 2, 2003.

(51) Int. Cl.
*G06F 17/00* (2006.01)

(52) U.S. Cl.
USPC .......................................................... 700/242

(58) Field of Classification Search
USPC ................................................. 700/242, 244
See application file for complete search history.

(56) References Cited

U.S. PATENT DOCUMENTS

| | | | |
|---|---|---|---|
| 4,478,658 A | 10/1984 | Wittwer | |
| 4,548,825 A | 10/1985 | Voss et al. | |
| 4,587,407 A | 5/1986 | Ahmed et al. | |
| 5,401,059 A | 3/1995 | Ferrario | |
| 5,468,110 A * | 11/1995 | McDonald et al. | 414/273 |
| 5,522,512 A * | 6/1996 | Archer et al. | 209/580 |
| 5,671,262 A * | 9/1997 | Boyer et al. | 377/11 |
| 5,700,998 A | 12/1997 | Palti | |
| 5,758,095 A | 5/1998 | Albaum et al. | |
| 5,845,255 A * | 12/1998 | Mayaud | 705/3 |
| 5,857,713 A | 1/1999 | Horimoto | |
| 6,112,182 A | 8/2000 | Akers et al. | |
| 6,150,942 A * | 11/2000 | O'Brien | 340/573.1 |
| 6,202,923 B1 * | 3/2001 | Boyer et al. | 235/375 |
| 6,370,841 B1 * | 4/2002 | Chudy et al. | 53/411 |
| 6,625,952 B1 * | 9/2003 | Chudy et al. | 53/168 |
| 2001/0001144 A1 | 5/2001 | Kapp | |
| 2002/0032582 A1 * | 3/2002 | Feeney et al. | 705/2 |
| 2002/0069088 A1 | 6/2002 | Berg | |
| 2003/0050802 A1 | 3/2003 | Jay et al. | |
| 2003/0144883 A1 | 7/2003 | Fagerholm et al. | |
| 2004/0006490 A1 | 1/2004 | Gingrich et al. | |
| 2004/0006491 A1 | 1/2004 | Brown et al. | |
| 2004/0019502 A1 | 1/2004 | Leaman et al. | |

OTHER PUBLICATIONS

J.M. Smith Corporation, Informational Literature entitled "Workflow QS1," 1 page (2002).

* cited by examiner

*Primary Examiner* — Stefanos Karmis
*Assistant Examiner* — Michael E Butler
(74) *Attorney, Agent, or Firm* — Ostrolenk Faber LLP

(57) ABSTRACT

A system and method for electronic assistance in dispensing pharmaceuticals, utilizing software, hardware and barcode technology to yield error free, clinically correct, adjudicated prescriptions. The system is adaptive to the preferences of an authorized user, by being configurable on the basis of when and what type of warnings are given in particular circumstances, based on entries in a field, and whether the order can proceed. Additionally, the invention allows for automated and electronically assisted refilling of orders. The invention allows for tracking and monitoring of prescription orders through barcode labeling and scanning.

9 Claims, 10 Drawing Sheets

FIGURE 2

| DWF0013 | | | Order Status Display | | | | | 10/24// |
| | | | Company 1 NCS HEALTHCARE OF WICHITA | | | | | |
| Delivery Code | 1 Entered PCI/LTCP | 2 On List | 3 Held | 4 Pending Billing | 5 Reject Allowed | 6 Label | 7 Labeled | 8 Scanned | 9 Manifest |
| 1. STAT | 0/ | 0 | 0 | 0 | 0 | 0 | 0 | 0 | 12 |
| 2. RED | 0/ | 3 | 1 | 0 | 1 | 1 | 13 | 0 | 0 |
| 3. YELLOW | 0/ | 19 | 1 | 0 | 0 | 2 | 39 | 0 | 0 |
| 4. BLUE | 0/ | 3 | 0 | 0 | 0 | 0 | 20 | 0 | 0 |
| 5. GREEN | 0/ | 0 | 0 | 0 | 0 | 0 | 7 | 0 | 0 |
| 6. LINE | 0/ | 7 | 0 | 0 | 0 | 0 | 3 | 0 | 0 |
| 7. HOME | 0/ | 0 | 0 | 0 | 0 | 0 | 10 | 0 | 0 |
| 8. DEFAULT | 0/ | 0 | 0 | 0 | 0 | 0 | 0 | 0 | 0 |
| 9. CYCLE | 0/ | 0 | 0 | 0 | 0 | 0 | 127 | 5 | 0 |
| TOTAL | 0/ | 32 | 2 | 0 | 1 | 3 | 219 | 5 | 12 |

ENTER A COLUMN NUMBER TO DETAIL A STATUS, (R)EFRESH SCREEN, <ENTER> TO SEE MORE DELIVERY CODES, OR '/' TO EXIT ..

METHOD AND SYSTEM FOR ELECTRONIC ASSISTANCE IN DISPENSING PHARMACEUTICALS

CROSS-REFERENCE TO RELATED APPLICATION

This is a divisional of U.S. patent application Ser. No. 10/610,681, filed Jul. 2, 2003 in the name of John P. DiMaggio and entitled METHOD AND SYSTEM FOR ELECTRONIC ASSISTANCE IN DISPENSING PHARMACEUTICALS, the entire contents of which are incorporated herein by reference.

BACKGROUND OF THE INVENTION

Field of the Invention

The present invention relates to a method and system for electronic assistance in dispensing pharmaceuticals. More specifically, the invention is directed at providing a pharmaceutical dispensing system and method capable of insuring error free, clinically correct, adjudicated prescriptions. Once the system of the subject invention is created, the process of fulfilling, and refilling, a prescription order will be subject to electronic controls and assistance that allow for more efficiency, less error, and greater safeguards. Furthermore, the system of the subject invention will allow for monitoring and tracking of orders, and ensures that no orders are overlooked or delivered to the wrong facility.

In the past, there have been inefficiencies in traditional pharmaceutical dispensing methods, which utilized pharmacists to perform a physical check of an order or item. These dispensing methods were subject to human error that resulted in potential patient harm, inefficiency, confusion as to the adjudication of the order, and inaccuracy in the order.

The implications of error in dispensing items from a pharmacy can be quite severe. When a recipient is given a prescription item in error, there is at least a likelihood that the prescription item will not fulfill the purpose that the correct prescription item would have. Furthermore, there is a possibility that the prescription item received in error will cause the recipient to have an adverse reaction. Thus, the condition of a recipient may be harmed by the lack of treatment and possible adverse affects, which are contrary to the purpose of medical prescriptions.

Accordingly, it would be desirable to provide a system and method for dispensing pharmaceuticals capable of insuring error free, clinically correct, adjudicated prescriptions, order processing and monitoring. Further, it would be desirable to allow the system to be configurable based on an authorized user's preferences, allowing for greater efficiency and accuracy, easier administration of the system, and modifying tasks for a particular user or user group to carry out.

Additionally, it would be highly desirable to provide successful integration of such a dispensing system into existing pharmaceutical dispensing facilities through phased implementation, allowing for a smooth transition from current practices in dispensing to the system and method for dispensing pharmaceuticals of the subject invention. The first deliverable in the phased implementation will include a system capable of providing a clinical and financial order review prior to label printing. This first phase includes: 1) order processing modifications to separate the warning messages that different user groups may or may not respond to, and those that are not responded to in the order entry must be verified before a label is printed; 2) a pharmacist review or verification function, which allows a review of all new orders and any refills that have encountered a problem; 3) enhanced scanning capabilities, including refill and edit list scanning; 4) the financial review of the order including on-line adjudication; and 5) a function to monitor and display information about the position of all orders in the pharmaceutical dispensing facility (for example, orders entered, on list, RPh reviewed, on hold, rejected, printed, scanned, and manifest). The second deliverable in the phased implementation will incorporate a mandatory filling accuracy step achieved though order barcode scanning.

The terms "pharmacist," "Registered Pharmacist," and "RPh" may be used interchangeably throughout this specification, and are used to describe a health professional trained in the art of preparing and dispensing drugs and/or prescribed medical treatments.

The terms "prescription" and "Rx" may be used interchangeably throughout this specification, and are used to describe an order for the preparation and administration of a medicine or other treatment.

The difficulties, limitations and desires suggested in the preceding are not intended to be exhaustive, but rather are among many which demonstrate that prior art systems and methods for dispensing pharmaceuticals will admit to worthwhile improvement.

Objects of the Invention

It is, therefore, a general object of the invention to provide a system and method for dispensing pharmaceuticals, which utilizes software, hardware, and barcode technology to produce a process where prescriptions flow through pharmaceutical dispensing and electronically stop at quality gates, bypassing the need for dispensing pharmacists to conduct final physical checks of a product.

It is another general object of the invention to provide a system and method for reducing medication errors, utilizing barcode technology to monitor the processing of prescription orders and performing clinical checks in the processing of orders.

It is another general object of the invention to provide a system and method for ensuring full adjudication of pharmaceutical orders prior to label printing/shipment.

It is a specific object of the invention to provide a system and method to fulfill prescription orders, supporting automated methods for receiving prescription orders.

It is another specific object of the invention to provide a system and method for verifying prescriptions utilizing barcode technology, which is to be done by a pharmacist after data pertaining to an order has been entered into the system.

It is another specific object of the invention to provide a system and method for back end scanning prescription orders utilizing barcode technology, verifying that the correct item has been selected based on the label barcode and product barcode, and verifying that the item has been placed in the correct delivery tote.

It is another specific object of the invention to provide a system and method for monitoring a prescription order through the dispensing system, ensuring that every order proceeds to its ultimate conclusion without being overlooked. Also, it provides users with the ability to view information pertaining to the order in all phases of order fulfillment, and further allows for the customizable arrangement of the information.

It is another specific object of the invention to provide a system and method for configuring and enhancing the set up of the electronic interface, allowing for greater flexibility and customization of the system based on a user group, facility, pharmacy, and/or inventory.

It is another specific object of the invention to provide a system and method for providing information, based on a user group defined configuration, to determine the path a user takes through an order entry function to fill an order.

It is yet another specific object of the invention to provide a system and method for entering a prescription order, allowing an authorized user to configure which warnings are to be displayed and which must be responded with respect to fulfilling the order.

It is yet another specific object of the invention to provide a system and method for processing refill orders manually, performing checks based on time regulations and the quantity remaining for a prescription. The checks prompt warnings to the user if necessary. The information pertaining to the refill is stored, and the database is adjusted according to the transaction.

It is yet another specific object of the invention to provide a system and method for automatically refilling an order, allowing orders to be automatically refilled on a specific date determined through a number of criteria set by the user, and can be determined in the initial order entry.

It is yet another specific object of the invention to provide a system and method for automatically refilling orders, requiring no user input after entering prescription numbers if the system does not detect issues with the prescription.

It is a further object of the invention to provide a system and method for entering prescription numbers by manually typing the numbers, using a barcode reader, or by reading a list of numbers from a file.

It is a further object of the invention to provide a system and method for dispensing pharmaceuticals that is capable of being implemented in various phases, allowing for an easier transition from preexisting dispensing processes.

SUMMARY OF THE INVENTION

To achieve at least some of the foregoing objects, the subject invention provides a system and method for electronic assistance in dispensing pharmaceuticals. The present invention uniquely provides a method of dispensing prescriptions, utilizing the advantages of accuracy and efficiency built into the operation of barcode technology. Additionally, the capabilities of computer systems and software to process information, to be configured to particular preferences and to decrease human error are also utilized. The electronic dispensing system begins with an order entered into the system by a particular user, which may be a technician responsible for straight data entry. The technician enters basic information into the system, such as the facility, resident, drug, directions, quantity, days supply, issue date, number of refills, and the name of the physician. Warnings to be displayed or suppressed by the system during order entry are to be configured on a user group basis by an authorized user. Some warnings may arise during the data entry, which can be viewed by the technician, such as the physician having an invalid DEA number, the prescription being a duplicate drug, and possible refill conditions. Other warnings must be suppressed pending review by a pharmacist.

All new orders must be reviewed by a pharmacist, as well as certain refill orders. A pharmacist must be able to respond to all clinical warnings on the system before the order is verified. There are a multitude of warnings that a pharmacist may encounter, which are based on a series of checks the system performs consistent with the user group configuration. An order must be adjudicated so that it is determined that a "believable" payor is available, based on billing/coverage and adjudication checks. Once the pharmacist has verified an order and it has been adjudicated, it can be routed to the appropriate pharmaceutical dispensing area. A prescription label is to be generated once the order is verified by the pharmacist, and the order has been properly adjudicated.

All items that have been verified by a pharmacist and have been adjudicated have labels generated for them. When labels are generated they are routed to printers in the area of the pharmaceutical dispensing facility where the item is located. Therefore, all items have a bin location to which they are associated. The bin locations can be random, and do not have to be alphabetized by item name. Once the prescription label has been generated, the technician pulls the item from the appropriate bin location and labels the item.

All items dispensed must be scanned for accuracy using two scans. The first scan is done for pharmacy-to-delivery tote dispensing to ensure the order is going to the right nursing facility. The second scan is done for item-to-prescription dispensing to ensure that the right drug has been picked for the prescription. Once an item has been successfully scanned into the delivery tote, it will be available to print on a packing list. Before the delivery leaves, the pharmaceutical dispensing facility reviews all items entered, but not yet fully processed through the end of the workflow tracking system to ensure that all orders received have been fully processed.

DRAWINGS

Other objects and advantages of the present invention will become apparent from the following detailed description of preferred embodiments thereof taken in conjunction with the accompanying drawings, wherein:

FIG. 2 illustrates an order status screen;

Figure 3:
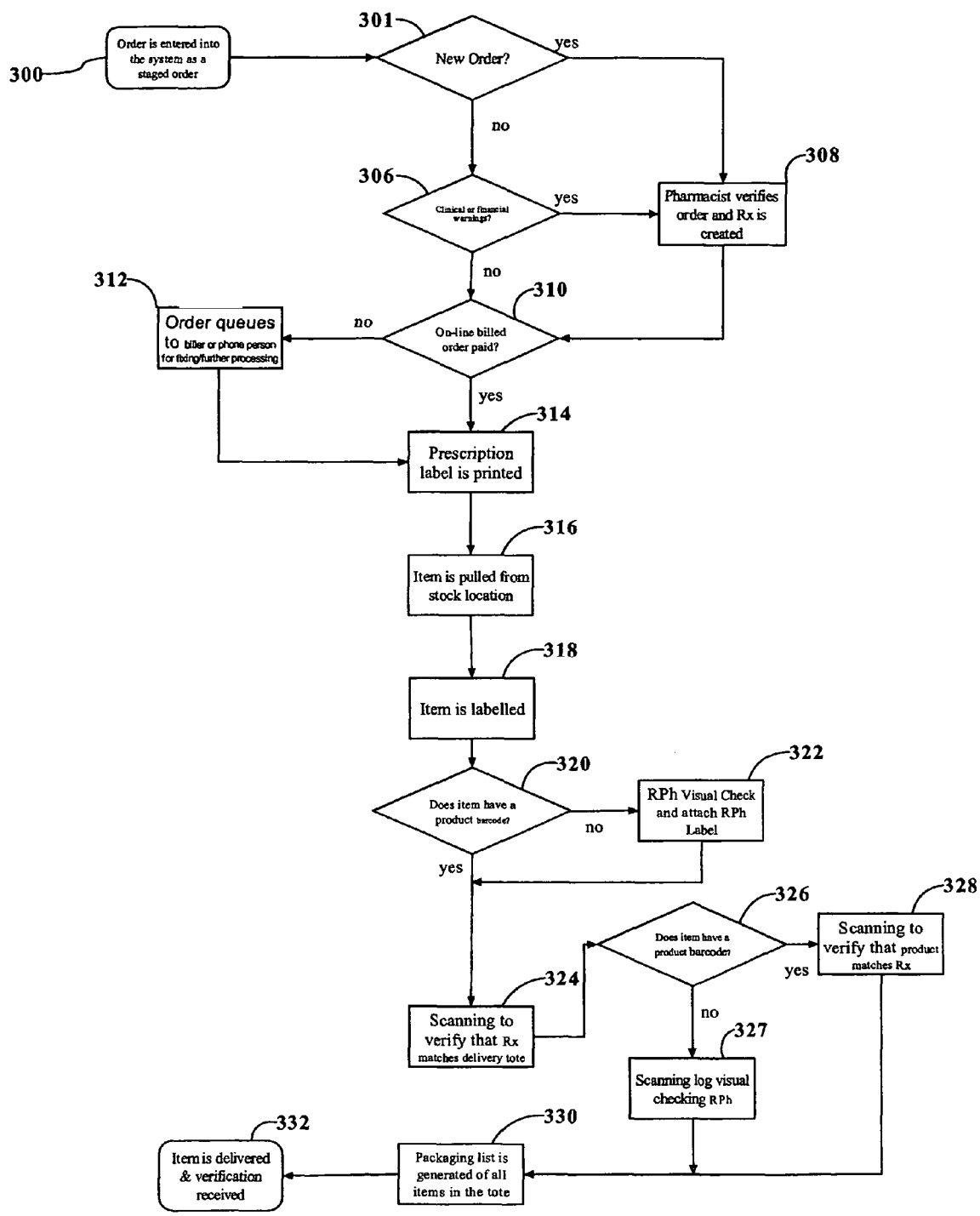
Figure 4:
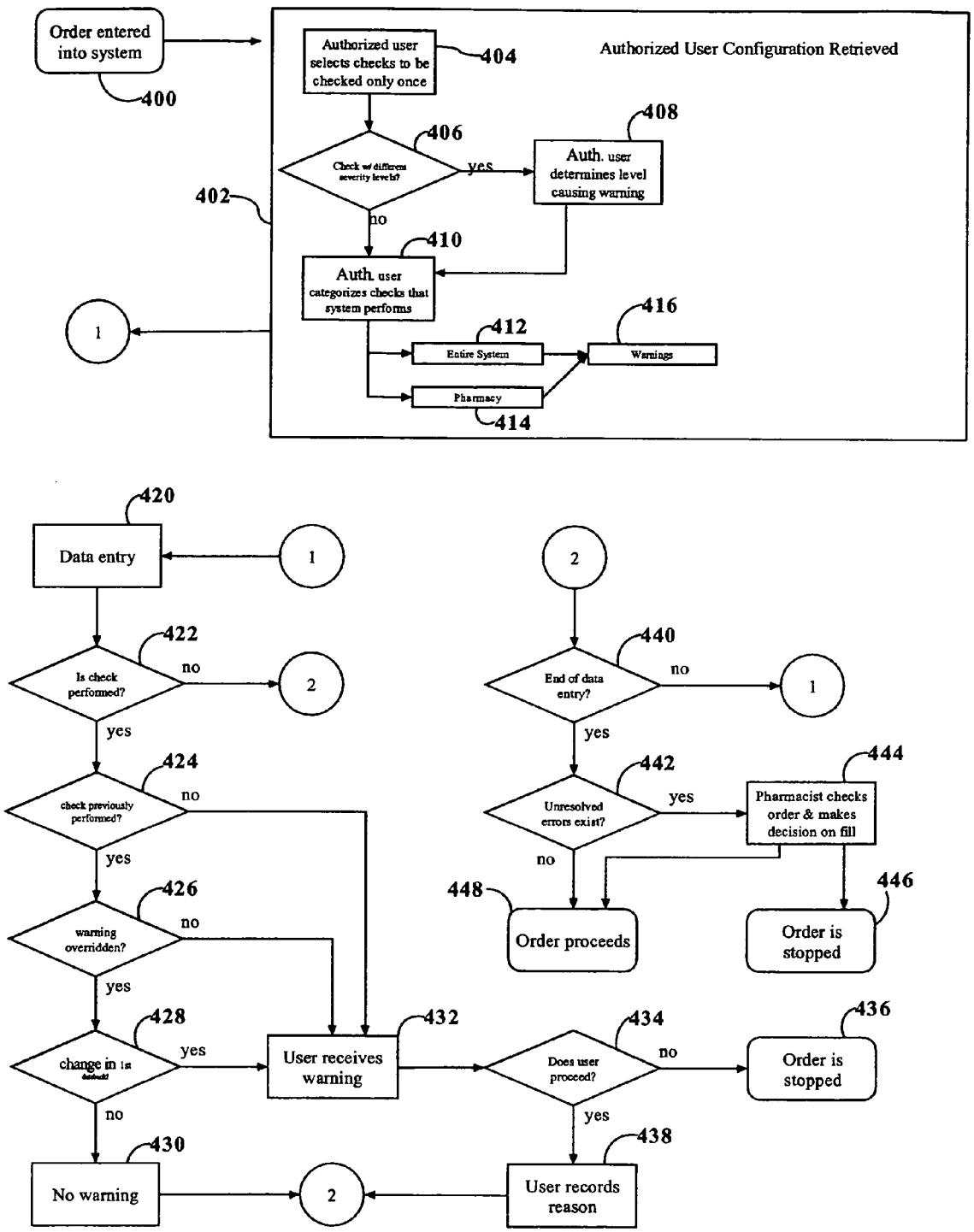
Figure 5A:
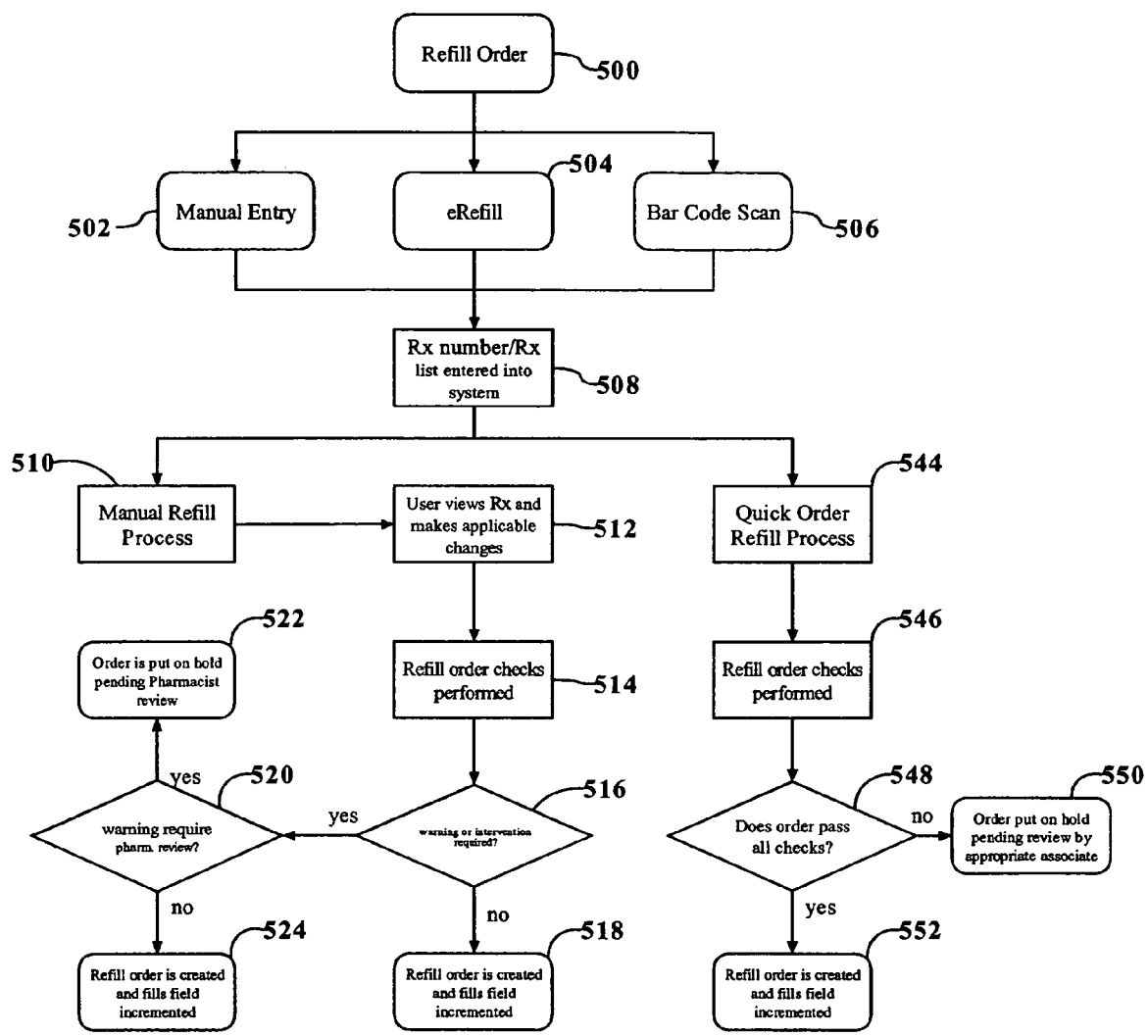
Figure 5B:
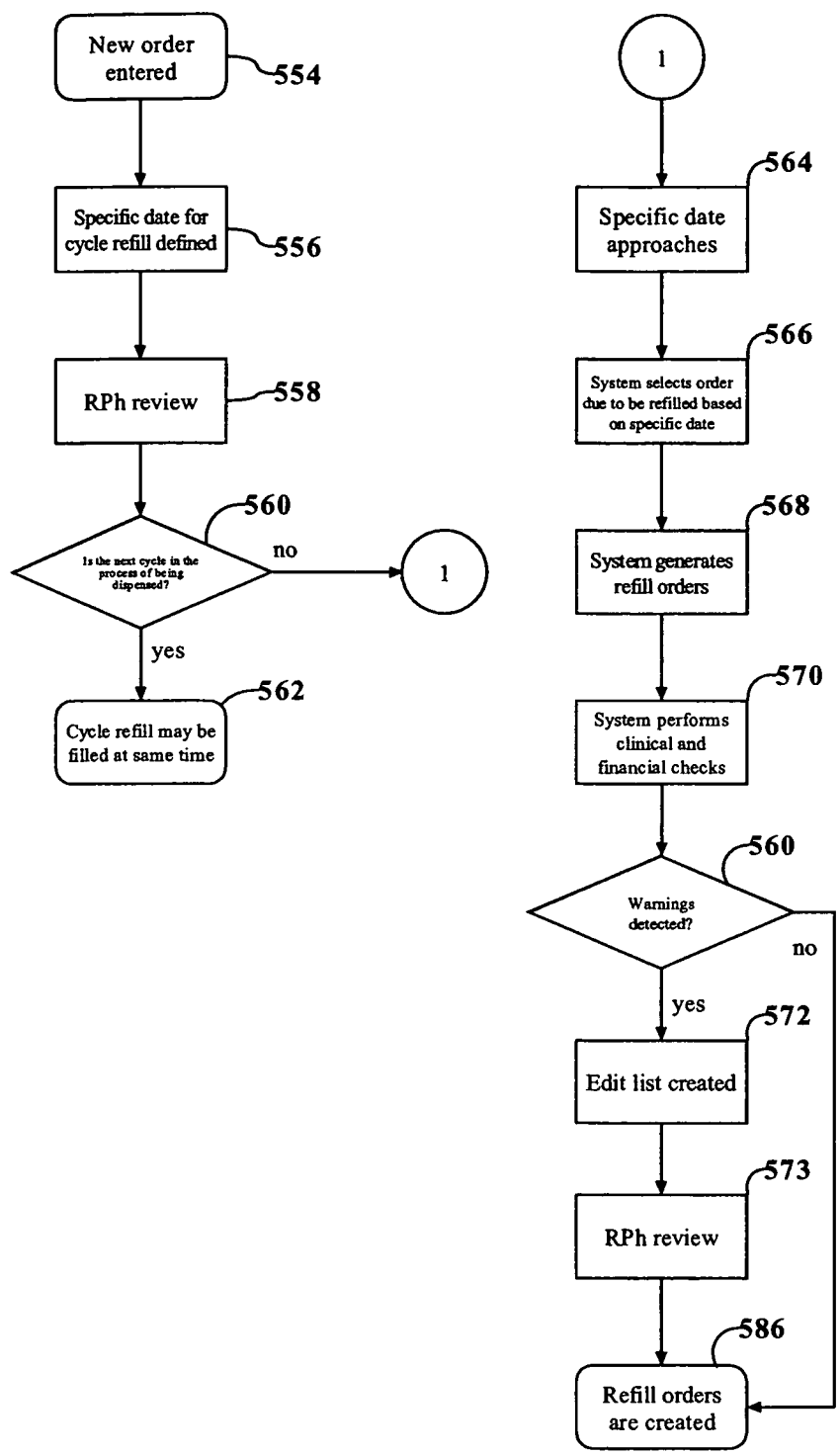
Figure 6:
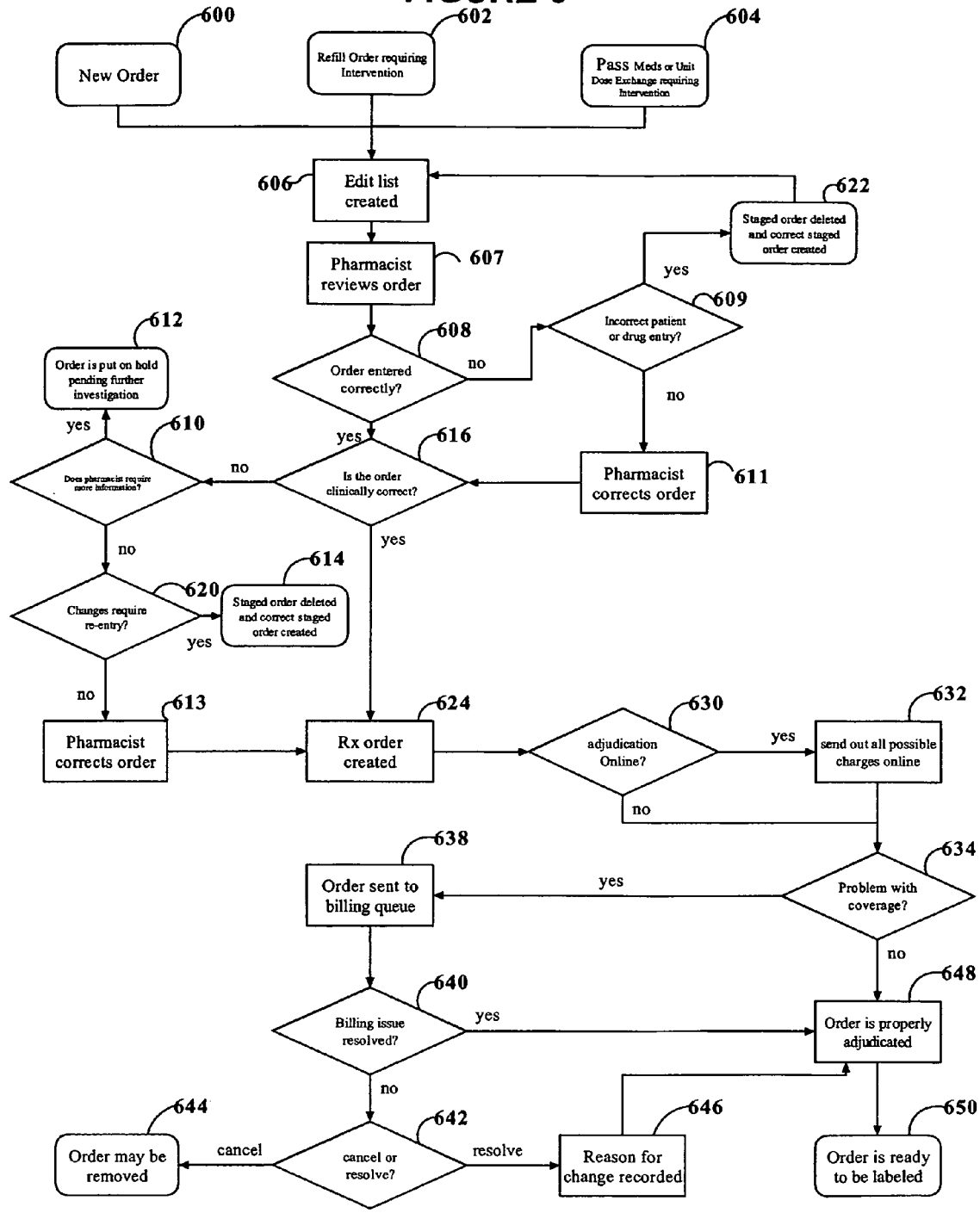
Figure 7:
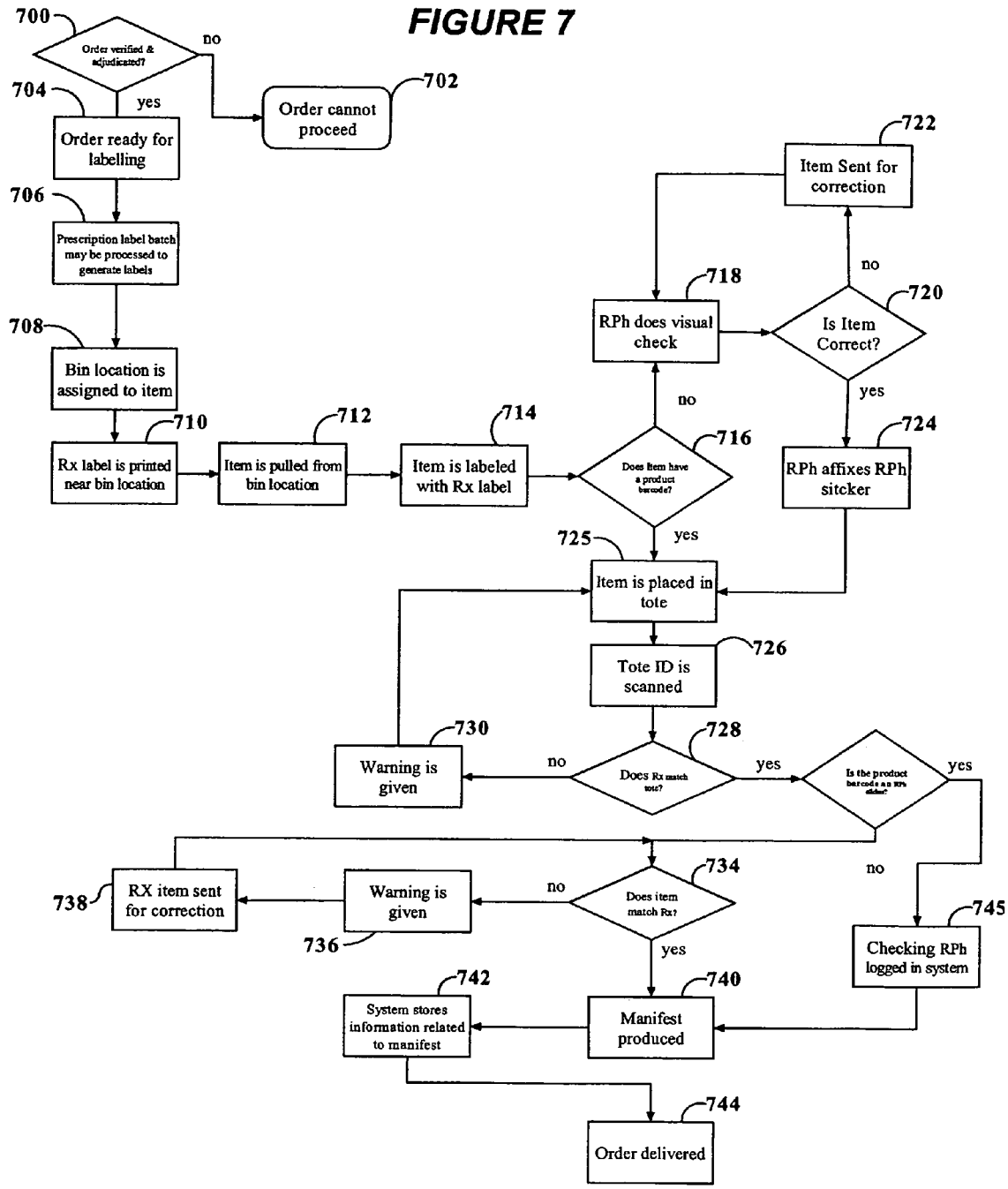
Figure 8B:
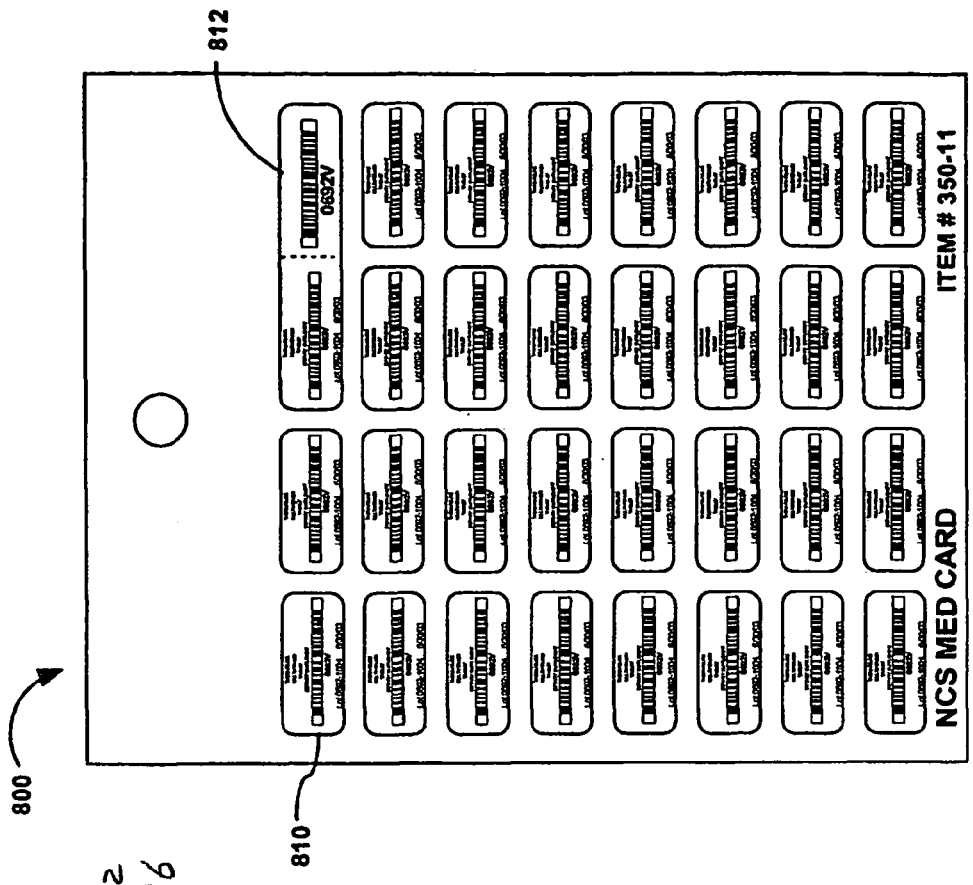
Figure 8A:
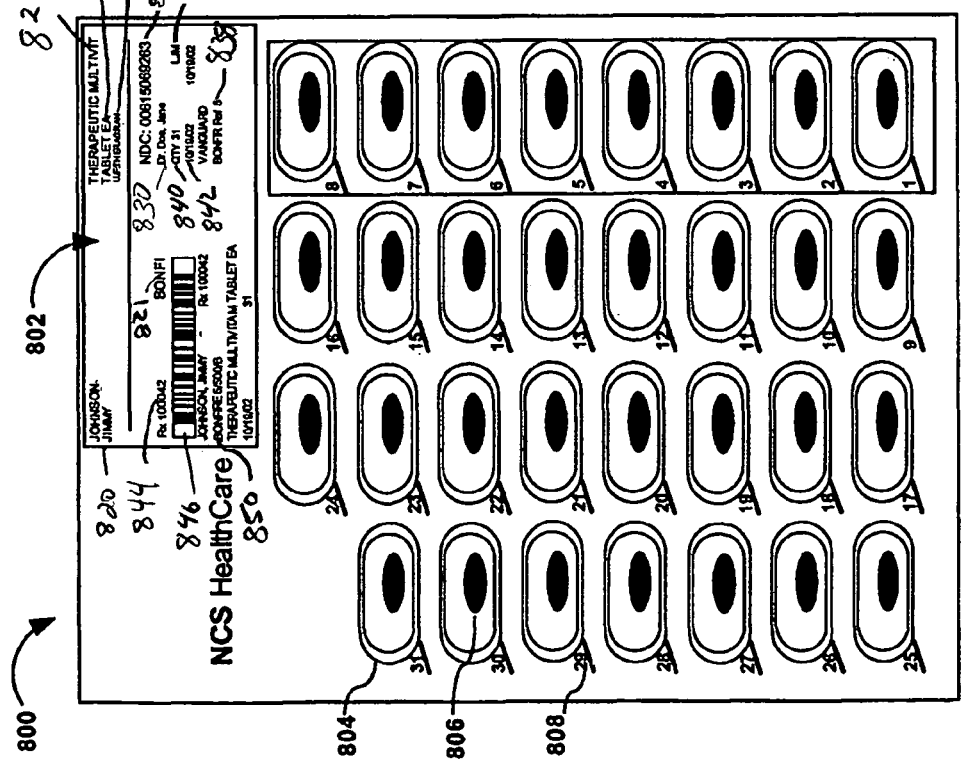

FIG. 3 provides a flowchart of the system for electronic assistance in dispensing pharmaceuticals;

FIG. 4 provides a flowchart of setting up the authorized user configuration and the general checks that are performed on each order processed through the system;

FIG. 5a is a flowchart illustrating how a refill order is processed through the system;

FIG. 5b is a flowchart illustrating the process of cycle refilling;

FIG. 6 is a flowchart illustrating pharmacist verification of an order;

FIG. 7 is a flowchart illustrating the system and method for labeling an item;

FIG. 8a is an illustrative example of the front side of a prescription card with a prescription label attached; and FIG. 8b is an illustrative example of the back side of a prescription card utilizing barcode technology.

DETAILED DESCRIPTION

Figure 1A:
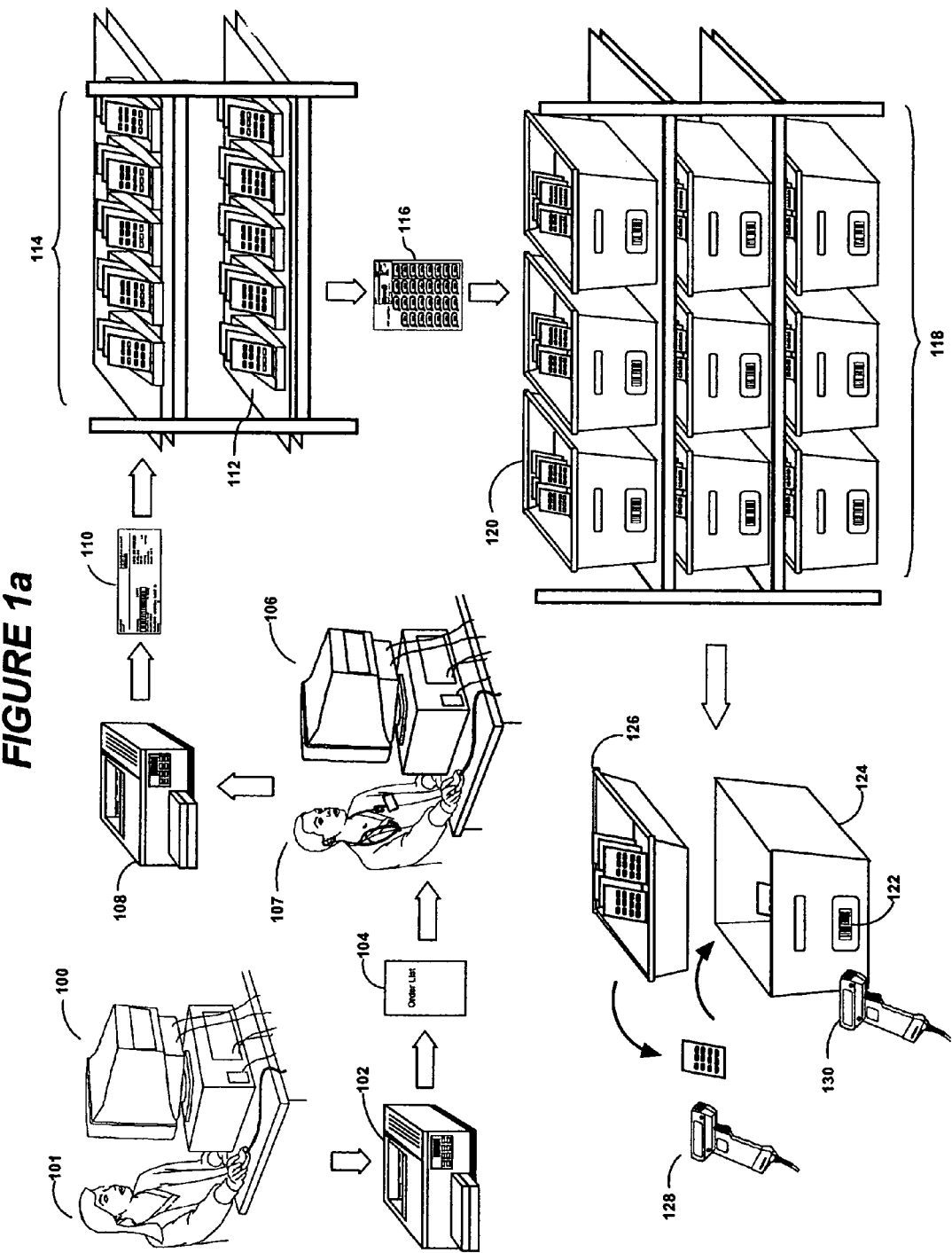
FIG. 1a illustrates an overview of the system for electronic assistance in dispensing pharmaceuticals.

The present invention is a system and method for electronic assistance in dispensing pharmaceuticals to increase dispensing efficiency, reduce error, and monitor orders. Referring to FIG. 1a, the system of electronic assistance in dispensing pharmaceuticals is shown from order entry to back end scanning. The system begins when an order entry technician 101 receives an order and enters the order into the system 100. The system creates a staged order that will not become an official Rx until clinically reviewed by a pharmacist. The order entry technician then sends a command to a printer 102 to create an edit list 104, containing all information from the order entry, any warnings, and other important information relayed by the system. Then, the edit list 104 and the original order are compared by a pharmacist 107 by visual check, barcode scan, and response to any warnings from the system. A pharmacist 107 may verify, make changes, delete or put an order on hold by entering such data into the system 106. If a pharmacist 107 verifies an order and the order is properly adjudicated, then the order is moved to a "label allowed" queue and is available to be printed. A technician can then send a command to a label printer 108 and a prescription label 110 is printed with an affixed barcode corresponding to the order (see FIG. 8c). A technician then takes a prescription label 110 from a label printer 108, retrieves a prescription 112 from a prescription bin 114, and attaches a prescription label 110 to a prescription card 116 containing the correct prescription. A technician then goes to a rack containing delivery totes 118, and places a prescription card 116 into the delivery tote 120 that correctly corresponds to an order (at this point a prescription card 116 is placed into the top of a delivery tote 120). Then, a technician will perform a delivery tote scan 130 of a barcode 122 on a bottom segment of a delivery tote 124. After scanning the barcode 122, the technician takes a prescription card 116 from a top segment of a delivery tote 126, performs a scan 128 of the prescription label 110 attached to a prescription card 116, performs a scan of the backside of the prescription card 116 containing a barcode identifying the medication (see FIG. 8b), and places the scanned prescription card 116 with attached prescription label 110 into a bottom segment of a delivery tote 124 if there are no scan errors. If there are scan errors (wrong drug, wrong tote), the prescription is set aside for a pharmacist review. The scan 130 of a barcode 122 on a bottom segment of a delivery tote 124 coupled with a scan 130 of the prescription label 110 attached to the prescription card 116 ensures that the correct order is in the correct delivery tote. The scan 128 of a prescription label 110 coupled with a scan 128 of the backside of the prescription card 116 ensures that a correct prescription order has been obtained. If the prescription has multiple pieces, all pieces must scan successfully to pass this quality step. Each piece of an order has a unique barcode prescription label 110 which prevents scanning a single piece multiple times. Both scans 130 and 128 together make sure that the order is ready for delivery with no errors. If there are no errors, the order will move to a "scanned" status signifying that the order has been filled correctly and is in the proper delivery tote.

Figure 1B:
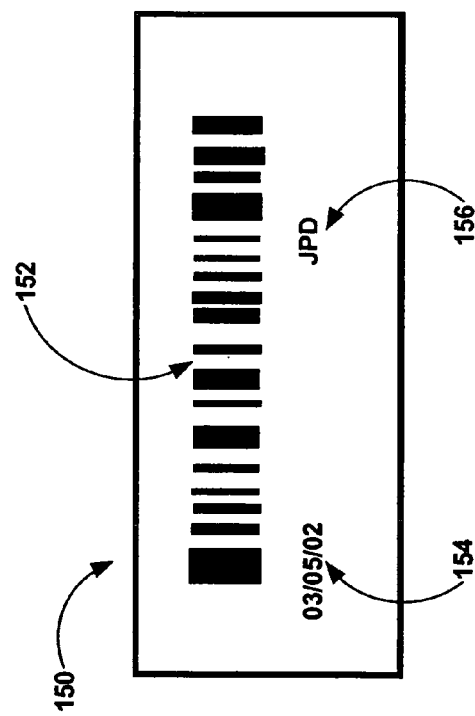
FIG. 1b is an illustrative example of an RPh label.

Alternatively, the use of a portable programmable barcode label generator is used when a product does not have a packaged or manufacturer barcode. Items with no barcode are placed aside for a pharmacist visual check. When the pharmacist verifies that the product is correct, he/she affixes a barcode label generated with the programmable label generator. The item is then placed in a nursing station tote along with other items to be scanned. When the technician scans these orders, they will scan the tote id, prescription label and the label generated with the label generator instead of the barcode on the product. Referring to FIG. 1b, a RPh label 150 is generated by the programmable label generator. The system recognizes the difference between a RPh label 150 and a product label when scanned with a barcode scanner. The system stores information to convey that a RPh performed a visual check in addition to a verifying RPh ID. This information is stored on the label 150 as opposed to the system verifying a product barcode. A label generator is programmed to include today's date, the RPh ID and a unique sequence number. The label 150 includes: 1) a unique barcode ID 152, which includes a RPh ID, the date, and a unique sequence number; 2) a date 154 in human readable form; and 3) a RPh's initials 156 in human readable form. This insures that the RPh label 150 can only be scanned on the day the label was printed and only scanned once per label (sequence number).

Referring to FIG. 2, an order status screen 200 is shown. An order status screen (workflow screen) 200 allows an user, such as a technician or pharmacist to monitor an order throughout the system. Once an order is entered into the system by a order entry technician it shows up on the screen in an "Entered" column 202. An order that is entered may then be printed to an edit list, which contains a barcode for the order and any warnings or other pertinent information that a pharmacist performing a verification may need. Once the order has been printed to an edit list, the status of the order shows up in an "On List" column 204. The edit list is compared to an original order by a pharmacist, by first performing a visual check and then scanning the edit list with a barcode reader. A pharmacist may release the order if no problems exist regarding an order's pharmaceutical accuracy, edit the order, delete, or hold an order if some problem exists. An order will be placed in a "Held" column 206 by the system if a pharmacist finds that a problem exists which requires a phone call or other clarification. If the order is released, the system assigns an official prescription number to the order. An order will be placed in a "Pending Billing" column 208 by the system if a pharmacist releases the order after verification and the payment is to be adjudicated between a billing person and a third-party payor. The order is then electronically billed to a third party payor. An order will be placed in a "Reject" column 210 by the system if a pharmacist releases an order, but the order is rejected by the third party. When an order is placed in the "Reject" column 210, a billing person will attempt to resolve the billing issue. An order will be placed in a "Label Allowed" column 212 by the system if a pharmacist releases an order and the payor is not a third party. An order will also proceed into the "Label Allowed" column 212 when an order has been properly adjudicated. When an order is in the "Label Allowed" column 212 the system allows a command to be sent to a label printer, a label is printed and the order moved to "Labeled" status column 214. A printed label is then taken by a technician, who retrieves the correct prescription from a bin, and the label is attached to the prescription and placed into the top segment of a delivery tote. Then, a technician takes a labeled prescription placed in the top segment of a delivery tote and scans the delivery tote, the prescription label, and the prescription (see FIGS. 1a, 3, and 7). Once scans are performed successfully for all pieces of the order, an order's status moves to a "Scanned" column 216, allowing a manifest, containing an order, to be printed. When a manifest has been printed the status of an order moves into a "Manifest" column 218. At this point an order is ready for delivery.

Other information is included on an order status screen 200. A "Delivery Code" column 220, which indicates a configured grouping of orders. The grouping can be a delivery route, a delivery time of day, or the type of order. Each row corresponds to the grouping of orders indicated by the individual categories of the "Delivery Code" column 220. A "Total" row 222 is displayed near the bottom of the screen, displaying and computing totals for each column. Also, a user command prompt 224 is located at the bottom of the order status screen 200, which allows the user to perform various functions related to the status of orders displayed.

Referring to FIG. 3, a flowchart of an overview of the electronically assisted workflow system for dispensing prescriptions is shown. First, an order for a prescription is entered into the system by a user, and a staged order is created (step 300). The system analyzes the order for clinical and financial warnings (step 306). The system analyzes whether the order is new (step 301). If the order is new, the Pharmacist must verify the order for data entry accuracy and any system detected warnings (step 308). If the order is not new, it is a refill, and the system analyzes the order for clinical and financial warnings (step 306). If the system determines that a clinical and/or financial warning exists with respect to the refill, the Pharmacist must verify the order for data entry accuracy and the system detected warnings (step 308). If the system determines that no warnings exist, the system proceeds to adjudication (step 310). In other words, the Pharmacist must only verify refill orders with system detected warnings. The system then analyzes whether the order can be adjudicated, i.e. whether there is a believable payor (step 310). If, the order is rejected, because the order cannot be adjudicated, the order then queues to a billing or phone person for appropriate changes and/or further processing (step 312). When changes are made by the billing or phone person (step 312), the system again analyzes whether the order has been adjudicated (step 310). Once the order is adjudicated then a prescription label is printed (step 314). Then, an item requested to fill the order is pulled from the stock location (step 316), and labeled (step 318). Then, a first analysis of whether the item has a product barcode is performed (step 320). During this first analysis, if the item does not have a product barcode, the order is set aside for a visual check by a Pharmacist who will affix a RPh label (FIG. 1b) to the order if Pharmacist deems the order has been filled properly (step 322). When an item has either a product barcode or a RPh label, scanning occurs to verify whether prescription matches the delivery tote (step 324). Then a second analysis of whether an item has a product barcode is conducted (step 326). If a product barcode exists, scanning occurs to verify that the product matches the prescription (step 328). If no product barcode exists for the item, scanning occurs to verify and log that a Pharmacist has visually checked orders without product barcodes (step 327). A packing list is then generated of all items in the tote that have successfully passed the scanning step (step 330). Finally, the system is complete when the item requested is delivered (step 332).

Setup Enhancements

Everyone who uses the system is set up as a user. Auditing and tracking is done by user code and system security is determined by user. In addition to setting up users, the system administrator is able to set up user groups, which are different classes of users sharing the same security and privilege levels. Furthermore, the system administrator is able to define the amount of interaction that a group of users will have in order entry. System administrators define which warnings appear, which fields are automatically stopped at, and which fields can be changed in order entry. The system may also be configured by place of service. User group configuration is further defined on a company level as well as on system-wide level. The system administrator can define by group the level of information that is displayed on the monitoring screen. For pharmacies, there is a system set up option which allows the system to be activated by company, so that an individual site can turn on the system at the point they are prepared to begin utilizing it.

Referring to FIG. 4, a flowchart illustrating how an authorized user (system administrator) configures the system and how checks are to be performed on orders being processed through the system. When an order is entered into the system by a user (step 400), the system retrieves the authorized user configuration to be used in processing the order (step 402).

The authorized user configuration is set at some time before a user enters the order. The authorized user selects checks that are to be performed only once (step 404), whether the check has different severity levels (step 406), and if so what level will cause a warning to occur (step 408), categorization of the checks that are performed (step 410), whether the configuration is for the entire system (step 412) or to be based on a pharmacy-by-pharmacy basis (step 414), and what action the warnings require (no action, action within thirty days, action by the end of the day, or immediate action) (step 416). The configuration can further be configured based on different user groups. For example, a data entry technician may receive different warnings or be prompted to enter data in different fields than a pharmacist.

Once, the authorized user configuration is set and retrieved by the system, the system is ready to perform checks on data entered into fields consistent with the configuration and the user or user group. For each field where data has been entered (step 420), the system determines whether a check is to be performed (step 422). If no check is to be performed on the data entry, a determination of whether there is any further data entry required is made (step 440). Then, the user may go to the next field, or if no other data is needed, onto the part of the system that determines if the order has any unresolved errors (step 442). If the check has not previously been performed the system may prompt a warning to the user consistent with the authorized user configuration (step 432). However, not all checks that are performed are intended to display a warning to every user group. For example, warnings not to be viewed by the data entry technician are to be viewed by the pharmacist verifying the order as unresolved errors. If the check has previously been performed (step 424), the user can opt to override the warning (step 426), otherwise the warning remains (step 432). If the user opts to override the warning, the system determines if a change has occurred in the databank (step 428). If a change has occurred in the databank, then the user receives a warning (step 432). If no change has occurred in the databank, then no warning is given (step 430). Then a determination of whether any other data is to be entered (step 440), and either the next field may have data entered into it, or, if no other fields require data, the system determines if the order has any unresolved errors (step 442). When a user receives a warning, the user decides whether to proceed (step 434). The order can either be stopped if the user does not wish to proceed (step 436). If the user opts to proceed with the order despite the warning, a reason for doing so is to be recorded into the system (step 438). At this point the user may go to the next field, or, if no other fields require data, the system determines if the order has any unresolved errors (step 442). If the system determines that the order has no unresolved errors, then the order proceeds to the next step in the system (step 448).

If the system determines that the order has additional unresolved errors requiring a Pharmacist intervention, (see FIG. 6) the Pharmacist makes the decision on the fill (step 444), where the order is either stopped (step 446) or proceeds (step 448).

In the preceding description of FIG. 4, a usual user group, data entry technicians, is expected to enter basic information such as the facility, resident, drug, directions, quantity, days supply, issue date, number of refills and physician. Some warning messages may be viewed by the data entry technician, such as the physician having an invalid DEA number, the prescription being a duplicate drug, and possible refill conditions. Other warnings are to be suppressed pending review by the pharmacist. Again, the decision on which warnings to display or suppress are configurable on a user or user group basis. Additionally, the specific checks that are performed as orders are entered into the system are clinical checks, billing/coverage checks, ordering and item checks, and substitution checks. The responses to these checks are tracked for auditing purposes.

Clinical checks are performed to reduce the possibility of medical error. The first clinical check to be performed is drug to drug interactions (item ordered interacts with other item(s) already on the patient's active profile). Interaction warnings indicate a degree of severity. Furthermore, drug interaction documentation is to be available on-line and include volume and page references. The next clinical check that is performed is duplicate therapeutic class (item being ordered is in the same therapeutic class as other item(s) already on the patient's active profile). Another clinical check that is performed is indications (whether the item being ordered is or is not indicated for any of the patient's diagnoses). A related check is then performed for contraindications (whether the item being ordered will adversely affect patient's listed diagnoses). The final clinical check that is performed is for allergies and cross-sensitivities (whether patient is allergic to the item being ordered, or whether the patient may exhibit a cross-sensitivity to the item being ordered).

The billing/coverage checks are as follows: 1) formulary checks, including inclusions and exclusions, and prior authorization requirements; 2) formulary coverage code restrictions; 3) capitation limits; 4) resident account information (check to see if the account is on hold or if it is a cash on delivery (COD) account); 5) on-line eligibility checks for resident or product coverage; and 6) resident order limits (order over number of prescriptions allowed, and order over dollar amount allowed). In terms of adjudication checks, if an order is covered by a third party, and that third party can be adjudicated on-line, the adjudication is done automatically after verification by a pharmacist.

The ordering and item checks begin with a check to determine if the order is already on the resident's active profile. If this is the case, the user is provided with the option to refill the current order, fill a duplicate new order, fill a new order and discontinue the old order, or not fill the order at all. The next check that is performed is whether the order is a Class 2, 3, 4, 5 order. If the order is a Class 2, 3, 4, 5 order the system checks whether the prescriber has a valid DEA number. The system then performs a check to determine if the physician is associated with the resident's facility. Next, the system checks whether an item being ordered is in a packaging form that is incompatible to the dispensing system for the station or financial plan parameters. Whether the item is part of the house stock is then checked. The facility's preference for receiving orders for this item is displayed. If the preferred packaging of the facility is available, the system indicates that package as a default, allowing the user to override the selection. The number of labels for the order must also be adjusted accordingly. This is configurable by facility, nursing station, room, or bed.

Substitution checks are the first type of checks that are performed. The first check is whether the product is eligible for therapeutic interchange. Next, a check is performed to determine whether the product is eligible for generic substitution. If these items are class A generics, the order does not need to be discontinued. Next, a check is performed to determine whether the product is not currently packaged in the preferred package size (of the patient, facility, or pharmacy). Then, a check is performed to determine whether the product is not on the formulary (of the facility, pharmacy, or resident). Finally, there is an automatic substitute item indicated on the inventory item, where the system allows an NDC number change as long as the two items are within the same generic class. If the item being ordered is subject to any of the above substitutions, the system automatically provides an alternative drug list.

Refill Order Processing

FIG. 5a is a diagram illustrating how a refill order is processed. A refill order 500 may be entered into the system by either: 1) an internet-based customer communication program for authorized customers (e.g., eAstral used by NCS) (step 504); or 2) a data entry technician manual entry (step 502), or through barcode scanning (step 506). Refills received via eAstral are processed automatically provided no interventions are required. Any refills that require interventions will appear on an edit list for review. Manual refills are processed through Quick Order Refill (batch) processing. The user must be able to enter a refill manually with a prescription number and then the order is to be refilled. If any intervention is required a warning is generated. If the warning requires a pharmacist review, the order is placed on an edit list pending a pharmacist verification. Barcode scanning is available for processing refills. If the refill label contains a barcode, it may be scanned into the system to process the refill order. It is an objective of the present invention to have all labels contain barcodes to speed refill processing.

Manual refill orders (step 510) have many of the same requirements as filling a new order, however, there are some differences. The system allows several options for entering the prescription number(s) being refilled (step 508). A user may type the prescription number(s) manually, use a barcode reader, or select orders from a profile list. Once the user enters the prescription number for a refill, the system automatically creates a refill order if the system determines that no warnings are to be displayed or responded to. The system performs all of the checks that it did when the order was filled for the first time. The checks that are performed are the billing and clinical checks (see FIG. 4 and above description of checks to be performed), as well as some additional checks (step 514). One additional check that is performed on refill orders is a check to determine if the refill has been ordered too soon, which is based on a system configuration threshold percentage of days. The system determines if there are any other warnings or interventions required (step 516). If there are no warnings or interventions required, there is no further interaction required by the user entering the order (order does not have to be displayed and no changes are to be made) (step 518). However, if the system detects a warning or intervention, the order is placed in an "on-list" status, and an edit list is created containing the list of warnings or interventions. A Pharmacist must then review the order (step 520) and either "release" the order, put the order "on-hold", change or delete the order. If the order is "released", the order will go though the normal billing/adjudication step. In summary, refills go through the same process as new orders with the exception that a Pharmacist intervention is required only if the system detects warnings or interventions. If the warning requires pharmacist review the refill order is put on hold pending the pharmacist review (step 522). If the warning does not require pharmacist review, the refill order is created and the fills field is incremented (step 524).

A batch refill (Quick Order Refill) (step 544) works in a way very similar to a manual refill. However, instead of letting the user view each prescription and make changes (step 512), the system automatically refills all of the prescriptions that do not have any warnings or require any interventions. There is no user input required after entering the prescription number(s) (step 508), except for those orders that require further review because problems have been found. The prescription number(s) can be entered the same as described above (typing number(s) manually, barcode scanning, and selecting from a list on a profile) (step 508). The system performs the refill order checks as described above (step 546). The system then determines if the order passes all checks (step 548). Orders that pass all checks are processed automatically (step 552), and orders that do not are printed on an edit list pending review by the appropriate associate (pharmacist review) (step 550).

Referring to FIG. 5b, automatic refilling (cycle refilling) encompasses automatically refilling routine orders based on a specific date. The process of cycle refilling begins when a new order is entered (step 554). The specific date for the cycle refill is determined through a number of means, established by the user during the initial order entry (step 556). For example, automatic refilling can be based on the anniversary date of an order, based on a cycle date, based on a days supply, based on the order date and the days supply, or based on a patient specific review date. When filling a new order, the system determines if the next cycle is in the process of being dispensed (step 560). If the next cycle is not in the process of being dispensed, a user initiates a refill generation function when the specific date for the cycle refill approaches (step 564). If the next cycle is in the process of being dispensed, the RPh has the option to refill the order at the same time as the verified first fill (step 562). For example, if an order is filled on Jan. 5, 2002 and the automatic refill orders are due to be delivered on Jan. 7, 2002, and the cycle fill for Jan. 7, 2002 is in process, the new order is filled for a two day supply and the system prompts the RPh that the automatic refill is due on Jan. 7, 2002. The RPh is given an option, when the first fill is verified, to fill the automatic refill for the order immediately and, if the user desires the automatic refill completed, the system automatically adds the second fill with the order date of Jan. 7, 2002 to the cycle fill workflow queue.

In the preferred embodiment the criteria for determining how the cycle refill date is determined is set up on a facility by facility, nursing station by nursing station basis, resident by resident basis, or item by item basis. Ultimately, the refill date and type of refill can be determined in the initial order entry (step 554). Most of the requirements for processing and checking automatic refill orders are the same as the batch and manual refilling methods. However, as the specific date of a cycle refill approaches, a user initiates a refill generation function for a facility or nursing station (step 564). The system selects orders due to be refilled based on the next cycle refill date (step 566). The system then generates the refill orders (step 568) and performs clinical and financial checks on all orders generated (step 570). Additionally, orders with a stop date past the next refill date are selected. The remaining processes are identical to the manual refill process: If the system detects any warnings or interventions, (step 571) an edit list is generated (step 572) and the order is placed in the "on-list" column pending a Pharmacist review (step 573). If the system does not detect any warnings or interventions, a refill order is created (step 586) and the order moves through the billing/adjudication step and on to scanning. Once the cycle refills are complete the system updates the information, showing the next time orders are due to be refilled.

Other means of filling prescription orders are available in the present invention. The Pass Meds processing feature allows leave of absence medications to be filled. A refill order is generated for each leave of absence medication and is immediately discontinued. A Pass Med is processed similar to a refill, and, thus, warnings are processed in the same manner as refill warnings. Additionally, the order also must be verified by a pharmacist if there has been a change in dose or frequency. The other method of filling a prescription is through Unit Dose Exchange processing. The pharmacy may batch process their exchange monthly or may drop the quantities used with the return of an exchange cart. Upon initial entry of an exchange order, the warnings are processed in the same manner as a new order. When the exchange drop or batch is processed, those exchanges must also be checked as refills and the pharmacist must verify the orders accordingly.

Verification

Referring to FIG. 6, a pharmacist must verify all new orders 600 entered into the system and refill orders 602 or any other processing (Pass Meds and Unit Dose Exchange) 604 that require intervention. The system places all new orders 600 and refill orders 602 with system detected warnings in the "On-List" column and edit lists are created (step 606). The edit list contains all pertinent information about the order including (but not limited to) facility name, patient name and age, allergies, drug, directions and a list of system detected warnings. A pharmacist performs a review of the order to verify that the order has been entered correctly and review any system warning to ensure clinical accuracy (step 607). A determination is made as to whether the order has been entered correctly (step 608). If the order has not been entered correctly, a determination of whether an order has been entered with the wrong patient or drug is made. (step 609). If the order has been entered with the wrong patient or drug, the RPH deletes the order and sends the order back to order entry for re-entry (step 622). If the patient and drug are correct, but other information in the order has been entered incorrectly, the RPh will make the necessary changes (step 611).

Once the order is entered correctly, the RPh then determines whether the order is clinically correct (step 616). If the order is not clinically correct, a determination of whether the pharmacist requires more information is made (step 610). If a clinical issue exists and the RPh required more information from a physician or the facility, the RPh will put the order on hold pending further investigation (step 612). If the pharmacist does not require further information, a determination is made as to whether the clinical issue(s) require the entire order to be re-entered (step 620). If the clinical issue(s) requires the entire order to be re-entered, the RPh deletes the order and sends it back to order entry for re-entry (step 614). If the clinical issue(s) does not require the order to be re-entered, the RPh will make the necessary changes (step 613), and the order is verified as being clinically correct.

Once the order is verified as being clinically correct, an RX order is created (step 624) and the order is removed from the RPh work queue. The system then determines if the order can be adjudicated online (step 630). If the order can be adjudicated online, all charges that may be sent online are transmitted (step 632). Once the orders that can be adjudicated online have been sent, the system then determines if there is a problem with the adjudication (coverage) (step 634). If there is a problem with the adjudication (coverage), the order is placed in a billing queue (step 638) for financial review and processing. If the order is placed into the billing queue, any billing issues must be resolved (step 640). If all financial issues have been resolved, the order is then properly adjudicated (step 648). If a rejected order cannot be resolved, the order must be cancelled or the facility must be contacted to determine a resolution (step 642). The billing personnel has their own verification function so that orders may be changed, cancelled, resubmitted on-line, or the responsible party may be changed. If a user changes the responsible party, a field is available for the user to enter a reason for the change of the responsible party (step 646), and the order is then properly adjudicated (step 648). If the rejected order cannot be resolved, the order may be canceled (step 644).

Once the order has been properly adjudicated (step 648) it is available for labeling (step 650). When an order proceeds from verification and adjudication, the order is placed in a "label allowed" queue for label printing in the next label print batch.

Packaging, Labeling, and Delivery

FIG. 7 is a flowchart illustrating how an item being ordered through the system is labeled and packaged. The system first determines whether an order has been verified and adjudicated (step 700). If the order has not been verified and adjudicated of the order cannot proceed (step 702). Once an order has been verified and adjudicated, the order is ready for labeling (step 704) and the prescription label batch may be processed to generate labels (step 706). A bin location is assigned to the item (step 708) and an Rx label is printed near the bin location (step 710). The item is pulled from its bin location (step 712), and labeled with an Rx label (step 714). Before placing an item in a delivery tote (step 725), the system determines whether an item has a product barcode (step 716). If the item does not have a product barcode, the RPh does a visual check of the item (step 718), and determines whether the item is correct (step 720). If the item is incorrect the item is sent for correction (step 722), and the RPh repeats the visual check (step 718) and determination of item correctness (step 720) on the corrected item. Once the item without a product barcode is correct, a RPh affixes a RPh sticker (step 724). An item with a product barcode or one that has went through the RPh's visual check and been affixed with an RPh sticker is then placed in a delivery tote (step 725). Then, tote label and the Rx label are scanned (step 726) to verify that the order is in the correct tote. Then, the drug item barcode is scanned to verify that the item matches the prescription (the correct drug has been selected based on the label barcode) (step 728). The system allows the tote to be scanned once and each item scanned individually. If the item does not match the prescription order, a warning is given (step 730), and the item is returned to stock. If the item does match in step S728, and the product barcode has the RPh sticker, then a checking of the RPh logged in the system occurs (step 745). The system also verifies if the prescription matches the delivery tote (step 734). If the prescription order does not match the delivery tote, a warning is given (step 736), and the prescription is set aside for a visual check by a RPh. The order is then placed in the correct delivery tote (step 738), scanning once again to verify the prescription matches the delivery tote (step 734).

Manifests (packing lists or delivery receipts) are produced (step 740) for all items that have passed the scanning checks. For those orders not completed information is provided as to why the order was processed but not filled by the pharmacy. Manifests accompany the orders and can be signed to verify that the orders were delivered and accepted. The system tracks when an order has been placed on a manifest. The system stores the date and time manifests are created, as well as the user who processed the manifest (step 742). A user may process a batch of manifests at various times throughout the day. Additionally, users are provided with various selection criteria in order to limit the items that appear on manifests in the batch: user code, facility, nursing station, patient, order date, drug class, label type, prescription number, and delivery time (priority code). Users can also have batch manifests sorted by user defined parameters. A user has the ability to reprocess a previously processed batch manifest (easily identified by batch number and available for a number of days as defined by the user). If a user does choose to reprocess a batch, he/she is also able to further limit the orders to print in a new batch manifest using the selection criteria indicated on a previously processed batch manifest. The system stores the batch number, description of the batch, list of orders in the batch, the barcode, and the manifest number (step 742). If a counseling sheet is required, it is generated at the time when the manifest is created so that it is delivered with the items on the manifest.

Once a manifest is produced (step 740), with accompanying counseling if necessary, and the system stores information related to a manifest (step 742), an order is ready to be delivered. An order is then delivered (step 744), and the order is accepted or rejected. If an order is accepted, a manifest is signed, verifying delivery and acceptance of an order.

Barcode Scanning and Monitoring

FIGS. 8*a* and 8*b* illustrate the front and back of a prescription card 800 respectively. Referring to FIG. 8*a*, once a prescription card 800 is pulled from a bin, a prescription label 802 is attached to the front, which is to correspond to an order in a "Labeled" status (see FIG. 2). The front of a prescription card 800 contains individually packaging 804 for each pill or medication 806, and has a number 808 corresponding to the order the medication is to be taken in and how many doses have been taken or corresponding to the day of the month the med is to be taken.

Referring to FIG. 8*b*, the back of a prescription card 800, each individual packaged dose contains a penetrable, information containing seal 810. A seal 810 contains a barcode for scanning if necessary, as well as other information pertaining to the medication, such as the expiration date, lot number, and name of medication. A barcode 812 appears in the top right region of the card, which does not correspond to an individual dose on the front side, and is used for scanning purposes to check for correct order and delivery.

Referring also to FIG. 8*a*, an illustrative example of a prescription label 802 using barcode technology is shown. Information pertaining to an order is contained on the prescription label 802. A patient's name 820, last name followed by first name, is contained at the top of the label 802 and under the barcode 846. An item's name and form 822 and 852 are contained at the top of a label 802 and a few lines below barcode 846. Information relating to a facility/nursing station is contained as an abbreviation 821 above barcode 846, as a facility/nursing station/room/bed 850 below the barcode, and as a facility/nursing station abbreviation followed by a number of refills 838. A brand name 826 of a prescription may be contained below a generic's name and form 822. A numeric code 828 relating to the NDC of the item ordered is also located on the label. A doctor's name 830 who prescribed the medication, the quantity 840, and the date of prescription 842 are contained on the label. A pharmacist's initials 832 are also included. A prescription number 844 is located above and below a barcode. Finally, a pharmaceutical manufacturer may be identified on prescription label 802. Barcode 846 represents the unique identification number of that label.

A barcode reading apparatus is used to scan the prescription labels that are generated, and then send the information from the scan into the system. The barcode 846, order number, contains a series of vertical lines of differing widths and spaces capable of relying information to the computer system when scanned.

FIG. 2 and its above description illustrates how users of the system are allowed to monitor/track orders throughout the entire system through the order status screen 200. Monitoring/tracking allows every order to proceed to its ultimate conclusion without being overlooked. A user tracks an order by viewing a monitor screen, such as an order status screen 200, which allows the user to see what is scheduled to be delivered, sorted by delivery route, and the status of the orders that are to make up the delivery. In addition to the description of the order status screen 200 in FIG. 2, all phases of order fulfillment are able to be tracked and available to be viewed on the monitor screen: remote order, order entry, pharmacist verification, labeling, filling, back end check, and delivery. The user is able to select which phases of order fulfillment are to be displayed on the monitor screen. Additionally, the system also provides a sortable, multileveled breakdown of orders based on criteria such as facility, priority code, delivery time, type of order, dispensing method, and inventory location. The information may be broken down on different screens as defined by the user (i.e., each screen showing different types of orders). The system displays the number of orders that are currently in each area of the order fulfillment queue. The user can then select one the numbers and the system will display the list of orders that makes up the total number.

Phased Implementation

Based on the impact that the workflow system described above will have on the way some pharmacies conduct business, the implementation of the workflow system is intended to be phased in. The first deliverable (phase 1) is to implement set up enhancement, such as authorized user configurations, user groups, and pharmacist verification. The pharmacist verification function will allow a review of all new orders and refills that have encountered a problem. Additionally, enhanced scanning capabilities are to be implemented, including the ability to scan in refill orders, and produce edit lists which can be scanned by RPhs during clinical verification. In addition, the first phase includes the on-line billing adjudication step which is required before a label can be printed. The second deliverable (phase 2) is to implement the product filling verification where the prescription, product and location are verified through barcode scanning.

Summary of Major Advantages of the Invention

After reading and understanding the foregoing description of preferred embodiments of the invention, in conjunction with the illustrative drawings, it will be appreciated that several distinct advantages of the subject system and method for electronic assistance in dispensing prescriptions.

One advantage of the present invention is that it utilizes a forced sequence of quality gates for clinical, financial, and filling accuracy.

Another advantage of the present invention is that it provides improvements in pharmacist efficiency by eliminating a final pharmacist drug-to-label check.

Yet another advantage of the present invention is that it reduces medication errors by reducing the human element of a pharmacist manual drug-to-label check.

Yet another advantage of the present invention is that it improves medical dispensing efficiency by ensuring that filling time is spent filling clinically correct, fully adjudicated orders.

A further advantage of the present invention is that it allows prescription orders to be adjudicated immediately and efficiently.

A further advantage of the present invention is the monitoring/tracking of prescription orders throughout the system to ensure that no order is overlooked, providing an audit trail (information pertaining to an order going through the system), and allowing users to promptly and efficiently respond to any problems that may arise.

In accordance with the foregoing, the present invention provides a system and method for electronic assistance in dispensing prescriptions. The present invention allows a system that increases efficiency, reduces error and allows monitoring of orders in dispensing prescriptions.

A prescription order is an order for pharmaceutical items such as medications, drugs, and other tangible medical treatment items. For purposes of the present invention, a prescription order can be processed through the dispensing system in a variety of ways. The first embodiment is a new order entry. The second embodiment is a refill order. The refill order can be further segmented into manual refills, batch refills (Quick Order Processing), and cycle refills (automatic refills). However, the aforementioned embodiments are not intended to be an exhaustive list of prescription orders processed through a dispensing system, rather these embodiments are illustrative.

In the present invention a pharmacy, nursing home, or other facility implements the system and method for dispensing pharmaceuticals.

The present invention is a method and system of dispensing pharmaceutical items that reduces medical error, increases prescription filling efficiency, and decreases on-line payor billing losses.

The present invention is a process for entering prescription orders into a computer system, which performs checks on the data entered corresponding the prescription order, prompting the user of any warnings or interventions that are required for that order.

The present invention is a method of verifying prescription orders entered into the computer system, ensuring that the orders are correctly dispensed.

The present invention is a process of adjudicating prescription orders entered into the system, checking for adequate coverage or a responsible payor and having the ability to quickly and efficiently adjudicate orders to the greatest extent possible online.

The present invention is a process of utilizing barcode technology on prescription labels, scanning to ensure correct prescription orders and correct delivery.

The present invention is a process of phased implementation, allowing for a smooth transition from existing dispensing methods to the present invention.

The present invention is carrying out the processes according to the present invention through a computer system configured by an authorized user, and utilizing barcode technology.

The present invention includes a computer system of a pharmaceutical dispensing facility capable of carrying out the processes according to the present invention, and a barcode scanner capable of reading and transmitting information from a barcode into the computer system.

In describing the invention, reference has been made to preferred embodiments and illustrative advantages of the invention. Those skilled in the art, however, and familiar with the instant disclosure of the subject invention, may recognize additions, deletions, modifications, substitutions and other changes that fall within the purview of the subject invention.

What is claimed is:

1. A method for electronically assisting in dispensing pharmaceuticals in one or more pharmacies, said method comprising the steps of:

configuring an electronic system to process a prescription order by:
defining how the system respectively operates for different users;
defining a check to be performed on the prescription order;
categorizing the check, and defining a number of times that the check is to be performed by the system as a function of the categorizing;
setting a severity level for the check and triggering a respective warning as a function of the severity level;

defining whether the check is to be performed on a pharmacy by pharmacy basis;

receiving, by the system, data from a user pertaining to the prescription order;

processing the prescription order and verifying that the prescription order is correct;

further comprising:

generating a prescription label having a first barcode associated with the prescription order, said prescription label identifying the required prescription medication, patient and a healthcare facility at which the patient is located;

retrieving prescription medication in accordance with the prescription label;

determining if the prescription medication has a second barcode associated therewith identifying the prescription medication and if so, scanning the second barcode to determine if the prescription medication corresponds to the prescription order; and if the prescription medication does not have a second barcode, having a qualified individual determine if the retrieved prescription medication is correct, and if so, generating a third barcode that is approved by the qualified individual and affixing the third barcode to the medication; said third barcode identifying the qualified individual who inspected the medication to determine that it is correct, the date of the inspection and a unique sequence number, said unique sequence number allowing the third barcode to be scanned only once on the date of the inspection.

2. The method of claim 1, further comprising implementing said system in phases.

3. The method of claim 1, wherein the step of configuring further comprises defining how the system respectively operates for a plurality of different user groups.

4. The method of claim 1, further comprising repeating the warning when the check is caused to be performed more than once.

5. The method of claim 4, further comprising enabling the user to override the warning.

6. The method of claim 1, wherein the step of configuring further comprises defining security and privilege levels for different users.

7. The method of claim 1, wherein the step of configuring further comprises defining an amount of interaction with the system that different users have.

8. The method of claim 1, wherein the step of configuring further comprises triggering a plurality of warnings as a function of the severity level.

9. The method of claim 1, wherein the step of configuring further comprises determining respective data entry fields that are available for data entry by a user.

* * * * *